United States Patent
Habtemariam et al.

(10) Patent No.: US 7,241,913 B2
(45) Date of Patent: Jul. 10, 2007

(54) RUTHENIUM COMPOUNDS

(75) Inventors: Abraha Habtemariam, Edinburgh (GB); Peter John Sadler, Penicuik (GB)

(73) Assignee: The University Court of the University of Edinburgh, Edinburgh (GB)

(*) Notice: Subject to any disclaimer, the term of this patent is extended or adjusted under 35 U.S.C. 154(b) by 80 days.

(21) Appl. No.: 10/554,271

(22) PCT Filed: Apr. 29, 2004

(86) PCT No.: PCT/GB2004/001837

§ 371 (c)(1),
(2), (4) Date: Oct. 24, 2005

(87) PCT Pub. No.: WO2004/096819

PCT Pub. Date: Nov. 11, 2004

(65) Prior Publication Data

US 2006/0258634 A1    Nov. 16, 2006

(30) Foreign Application Priority Data

Apr. 30, 2003  (GB) ................... 0309894.4

(51) Int. Cl.
*A61K 31/28*  (2006.01)
*C07F 15/00*  (2006.01)

(52) U.S. Cl. ........................... 556/137; 514/492

(58) Field of Classification Search ............ 556/137; 514/492
See application file for complete search history.

(56) References Cited

U.S. PATENT DOCUMENTS

| | | | |
|---|---|---|---|
| 4,980,473 A | 12/1990 | Barton | 546/10 |
| 6,750,251 B2 * | 6/2004 | Morris et al. | 514/492 |
| 6,936,634 B2 * | 8/2005 | Morris et al. | 514/492 |
| 6,979,681 B2 * | 12/2005 | Morris et al. | 514/188 |
| 2003/0023088 A1 | 1/2003 | Morris et al. | 546/2 |

FOREIGN PATENT DOCUMENTS

| | | |
|---|---|---|
| EP | 0 916 637 | 5/1999 |
| WO | WO 01/30790 | 5/2001 |
| WO | WO 02/02572 | 1/2002 |
| WO | WO 2004/005304 | 1/2004 |

OTHER PUBLICATIONS

Aird et al., "In vitro and in vivo activity and cross resistance profiles of novel ruthenium (II) . . . " Brit. J. of Cancer 86:1652-1657, 2002.

Allardyce et al., "Ruthenium in medicine: Current clinical uses and future prospects" Platinum Metals Rev. 45(2):62-69, 2001.

Ammar et al., "Synthesis of bis-oxazoline-ruthenium(II)-arene complexes. Combined catalytic . . . " J. of Organ. Chem. 662:63-69, 2002.

Bennet et al., "Mono-and bis-(acetylacetonato) complexes of arene-ruthenium(II) and arene-osmium(II) . . . " Can. J. Chem. 79:655-669, 2001.

Carmona et al., "Synthesis, X-ray structure, and nuclear magnetic resonance . . . " J. Chem. Soc., Dalton Trans. 1463-1476, 1990.

Carmona et al., "Heterobi-and Heterotetranuclear RuRh and RuIr complexes . . . " Organometallics 14:2066-2080, 1995.

Chen et al., "Organometallic ruthenium(II) diamine anticancer complexes: . . . "J. Am. Chem. Soc. 124(12):3064-3082, 2002.

Clarke et al., "Non-platinum chemotherapeutic metallopharmaceuticals" Chem. Rev. 99:2511-2533, 1999.

Dale et al., "Studies on DNA damage and induction of SOS repair by novel multifunctional bioreducible . . . " Anti-Cancer Drug Design 7:3-14, 1992.

Davies et al., "(Arene)ruthenium complexes with Bis(oxazolines): . . . " Organometallics 20:3029-3034, 2001.

Everaere et al., "(β-Amino alcohol)(arene)ruthenium(II)-catalyzed asymmetric transfer hydrogenation . . . " Eur. J. Org. Chem 275-291, 2001.

Faller et al., "Highly enantioselective Diels-Alder catalysis with a chiral ruthenium bisoxazoline . . . " J. of Org. Chem. 630:17-22, 2001.

Garcia et al., "Reactivity of [{($\eta^6$-arene)RuCl($\mu$-Cl)}] towards some potentially bidentate ligands . . . " J. of Org. Chem. 467:119-126, 1994.

(Continued)

*Primary Examiner*—Porfirio Nazario-Gonzalez
(74) *Attorney, Agent, or Firm*—Curatolo Sidoti Co. LPA

(57) ABSTRACT

Ruthenium (II) compounds of formula (I) are useful in the treatment and/or prevention of cancer

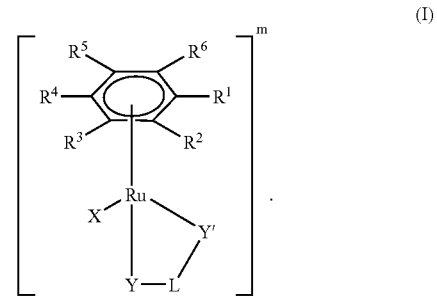

14 Claims, No Drawings

OTHER PUBLICATIONS

Gotze et al., "Separation of aminoacidato ruthenium(II) complexes by ion-pair chromatography" Fresenius J. Anal Chem. 346:634-638, 1993.

Guo et al., "Chelate ring-opening ruthenium complexes: A-ray crystal structure . . . " Inorganica Chimica Acta 273:1-7, 1998.

Habtemariam et al., Poster Presentation "Organometallic ruthenium arene anticancer complexes: structure-activity relationships" EUROBIC7, Garmisch, Germany, Aug. 29-Sep. 2, 2004.

Habtemariam et al., Poster Presentation "Structure-activity relationships for organometallic ruthenium arene complexes" ISBOMC'02, Paris, Jul. 18-20, 2002.

Habtemariam et al., Poster Presentation "Organometallic ruthenium arene complexes: structure-activity relationships" 1st Europ. Conference on Chemistry for Life Sciences, Rimini, Italy Oct. 4-8, 2005.

Kramer et al., "Organometallic half-sandwich complexes promote the formation of linear . . . " Chem. Eur. J. 2(1):1518-1526, 1996.

Kurosawa et al., "Second sphere coordination behaviour of aquo and amine ligands bound to . . . " Inorganica Chimica Acta 270:87-94, 1998.

Miyaki et al. "Synthesis and reaction of ruthenium(II) complexes containing heteroatom donor . . . " Inorganica Chimica Acta 300-302:369-377, 2000.

Morris et al., "Inhibition of cancer cell growth by ruthenium(II) arene complexes" J. Med. Chem. 44:3616-3621, 2001.

Ohnishi et al., "Coordination behavior of ruthenium(II) complexes with alcohol ligand . . . " Chem. Letters 809-810, 1999.

Sadler, P.J., "Ruthenium arene anticancer complexes" Second Int'l. Conference on Bioorganometallic Chem, Zurich Jul. 14-17, abstract p KL-1, 2004.

Sava, G., "Ruthenium compounds in cancer therapy" Ed. By Fricker, S.P., Chapman and Hall, London, pp. 65-91, 1994.

Sheldrick et al., "Synthesis and structural characterization of $\eta^6$-arene-ruthenium(II) complexes . . . " J. of Organo. Chem. 377:357-366, 1989.

Simal et al., "Ruthenium complexes containing diamine-based ligands as catalysts for insertion . . . " Tetrahedron letters 40:63-66, 1999.

Stern et al., "The use of macrocyclic and polydentate ligands in ruthenium organometallic chemistry" J. of Organo. Chem. 593-594:86-95, 2000.

* cited by examiner

RUTHENIUM COMPOUNDS

CROSS-REFERENCE TO RELATED APPLICATIONS

This application is the National Stage if International Application No. PCT/GB2004/001837, filed Apr. 29, 2004, which claims the benefit of Great Britain Patent Application Ser. No. 0309894.4, filed on Apr. 30, 2003. The contents of both applications are hereby incorporated by reference in their entireties.

This invention relates to ruthenium(II) compounds, to their use in medicine, particularly for the treatment and/or prevention of cancer, and to a process for their preparation.

Certain ruthenium(II) complexes have been proposed for use in treating cancer. For example, U.S. Pat. No. 4,980,473 discloses 1,10-phenanthroline complexes of ruthenium(II) and cobalt(III) which are said to be useful for the treatment of tumour cells in a subject.

Some other ruthenium(II) and ruthenium(III) complexes which have been shown to exhibit antitumour activity are mentioned in Guo et al, *Inorganica Chimica Acta*, 273 (1998), 1–7, specifically trans-[RuCl$_2$(DMSO)$_4$], trans-[RuCl$_4$(imidazole)$_2$]$^-$ and trans-[RuCl$_4$(indazole)$_2$]$^-$. Clarke et al have reviewed the anticancer, and in particular the antimetastatic, activity of ruthenium complexes: *Chem. Rev.*, 1999, 99, 2511–2533. Also, Sava has reviewed the antimetastatic activity in "Metal Compounds in Cancer Therapy" Ed by S P Fricker, Chapman and Hall, London 1994, p. 65–91.

Dale et al, *Anti-Cancer Drug Design*, (1992), 7, 3–14, describes a metronidazole complex of ruthenium(II) ie, [(η$^6$-C$_6$H$_6$)RuCl$_2$(metronidazole)] and its effect on DNA and on *E. coli* growth rates. Metronidazole sensitises hypoxic tumour cells to radiation and appears to be an essential element of the complexes of Dale et al. There is no indication in Dale et al that the complexes would be at all effective in the absence of the metronidazole ligand.

Krämer et al, *Chem Eur J.*, 1996, 2, No. 12, p. 1518–1526 discloses half sandwich complexes of ruthenium with amino esters.

Bennett et al, *Canadian Journal of Chemistry*, (2001), 79, 655–669 discloses certain ruthenium(II) complexes with acetylacetonate ligands.

Oro et al, *J Chem Soc, Dalton Trans*, (1990), 1463 describes ruthenium(II) complexes containing η$^6$-p-cymene and acetylacetonate ligands.

Our copending application GB 0215526.5 describes ruthenium(II) compound containing a bidentate ligand bearing an overall negative charge.

Chen et al, *J. Am. Chem. Soc.*, volume 124, no 12, 3064, (2002), describes the mechanism of binding of ruthenium complexes to guanine bases. The binding model requires NH bonds from a diamino ligand to be present in the complex for hydrogen bonding to the guanine base. Similarly, Morris et al, *J. Med. Chem.*, volume 44, 3616–3621, (2001), describes the selectivity of ruthenium(II) complexes for binding to guanine bases.

WO 01/30790 discloses ruthenium(II) compounds and their use as anticancer agents.

WO 02/02572 also discloses ruthenium(II) compounds that have activity against cancer cell lines. Complexes are disclosed containing a bidentate ligand which is a neutral diamine ligand.

Garcia et al, *Journal of Organometallic Chemistry*, 467 (1994), 119–126 discloses the preparation of [(η6-arene)Ru (o-phenylenediamine)Cl]PF$_6$ wherein arene is benzene or p-cymene.

There exists a need for novel anti-cancer compounds which can be used as alternatives to the compounds which are currently available.

In particular, there exists a need for compounds which can have a different profile of activity against different types of tumour cells and/or which can exhibit activity against cells that are resistant to other anti-cancer agents (such as adriamycin).

The present invention provides a novel class of ruthenium (II) complexes having anti-tumour activity.

According to the present invention, there is provided a ruthenium(II) compound of formula (I):

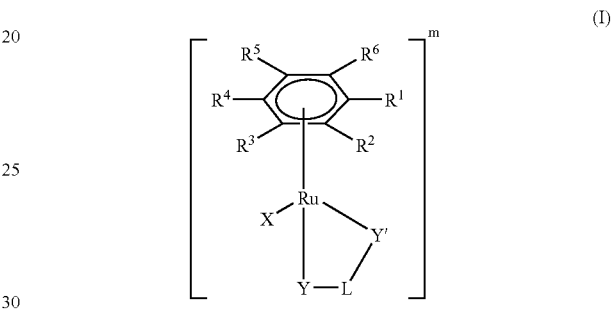

(I)

wherein: R$^1$, R$^2$, R$^3$, R$^4$, R$^5$ and R$^6$ independently represent H, (C$_1$–C$_6$)alkyl, (C$_2$–C$_6$)alkenyl, (C$_2$–C$_6$)alkynyl, hydroxy (C$_1$–C$_6$)alkyl, amino(C$_1$–C$_6$)alkyl, halo, hydroxyl, CO$_2$R$^7$, CONR$^8$R$^9$, COR$^{10}$, SO$_3$H, SO$_2$NR$^{11}$R$^{12}$, aryloxy, (C$_1$–C$_6$) alkoxy, (C$_1$–C$_6$)alkylthio, —N=N—R$^{13}$, NR$^{14}$R$^{15}$, aryl or aralkyl, which latter two groups are optionally substituted on the aromatic ring by one or more groups independently selected from (C$_1$–C$_6$)alkyl, (C$_2$–C$_6$)alkenyl, (C$_2$–C$_6$)alkynyl, hydroxy(C$_1$–C$_6$)alkyl, amino(C$_1$–C$_6$)alkyl, aryl, aralkyl, halo, hydroxyl, CO$_2$R$^{7a}$, CONR$^{8a}$R$^{9a}$, COR$^{10a}$, SO$_3$G, SO$_2$NR$^{11a}$R$^{12a}$, aryloxy, (C$_1$–C$_6$)alkoxy, (C$_1$–C$_6$) alkylthio, —N=N—R$^{13a}$, NR$^{14a}$R$^{15a}$, or R$^1$ and R$^2$ together with the ring to which they are bound represent a saturated or unsaturated carbocyclic or heterocyclic group containing up to three 3- to 8-membered carbocyclic or heterocyclic rings, wherein each carbocyclic or heterocyclic ring may be fused to one or more other carbocyclic or heterocyclic rings, and wherein each of the rings may be optionally substituted by one or more groups independently selected from (C$_1$–C$_6$) alkyl, (C$_2$–C$_6$)alkenyl, (C$_2$–C$_6$)alkynyl, hydroxy(C$_1$–C$_6$) alkyl, amino(C$_1$–C$_6$)alkyl, aryl, aralkyl, halo, hydroxyl, CO$_2$R$^{7b}$, CONR$^{8b}$R$^{9b}$, COR$^{10b}$, SO$_3$G', SO$_2$NR$^{11b}$R$^{12b}$, aryloxy, (C$_1$–C$_6$)alkylthio, —N=N—R$^{13b}$, NR$^{14b}$R$^{15b}$ or (C$_1$–C$_6$)alkoxy;

one or more of R$^1$ to R$^6$ optionally being covalently bonded via a carbon-carbon, carbon-nitrogen or carbon-oxygen bond to another R$^1$ to R$^6$ group on another compound of formula (I);

R$^7$, R$^8$, R$^9$, R$^{10}$, R$^{11}$, R$^{12}$, R$^{13}$, R$^{14}$, R$^{15}$, R$^{7a}$, R$^{8a}$, R$^{9a}$, R$^{10a}$, R$^{11a}$, R$^{12a}$, R$^{13a}$, R$^{14a}$, R$^{15a}$, R$^{7b}$, R$^{8b}$, R$^{9b}$, R$^{10b}$, R$^{11b}$, R$^{12b}$, R$^{13b}$, R$^{14b}$ and R$^{15b}$ are independently selected from H, (C$_1$–C$_6$)alkyl, aryl or aralkyl;

X is a neutral or negatively charged O-, N- or S-donor ligand or halo; G and G' are independently selected from alkali metals, aryl, aralkyl and (C$_1$–C$_6$) alkyl;

Y is $NR^{16}R^{17}$ and Y' is $NR^{18}R^{19}$, wherein $R^{16}$, $R^{17}$, $R^{18}$ and $R^{19}$ are independently selected from H, $(C_1–C_6)$alkyl, aryl or aralkyl;

L is 1,2-arylene, 1,2-$(C_5–C_8)$cycloalkylene or $(C_2–C_6)$alkylene, provided that when L is $(C_2–C_6)$alkylene, one of $R^{16}$ and $R^{17}$ is covalently bonded to one of $R^{18}$ and $R^{19}$ such that they form with L a ring containing Y and Y', said 1,2-arylene, 1,2-$(C_5–C_8)$cycloalkylene and $(C_2–C_6)$alkylene groups being optionally fused with one or more saturated or unsaturated carbocyclic or heterocyclic groups containing up to three 3- to 8-membered carbocyclic or heterocyclic rings, wherein each carbocyclic or heterocyclic ring may be fused to one or more other carbocyclic or heterocyclic rings, said 1,2-arylene, 1,2-$(C_5–C_8)$cycloalkylene and $(C_2–C_6)$alkylene groups and/ or the groups to which they are fused being optionally substituted with one or more groups independently selected from $(C_1–C_6)$alkyl, $(C_2–C_6)$alkenyl, $(C_2–C_6)$alkynyl, hydroxy$(C_1–C_6)$alkyl, amino$(C_1–C_6)$alkyl, halo, hydroxyl, nitro, $CO_2R^{7'}$, $CONR^{8'}R^{9'}$, $COR^{10'}$, $SO_3H$, $SO_2N\ R^{11'}R^{12'}$, aryloxy, $(C_1–C_6)$alkoxy, $(C_1–C_6)$alkylthio, $—N{=}N—R^{13'}$, $NR^{14'}R^{15'}$, aryl or aralkyl, and having one or more $CH_2$ groups optionally replaced by $C{=}O$ groups, wherein $R^{7'}$, $R^{8'}$, $R^{9'}$, $R^{10'}$, $R^{11'}$, $R^{12'}$, $R^{13'}$, $R^{14'}$ and $R^{15'}$ are independently selected from H, $(C_1–C_6)$alkyl, aryl or aralkyl;

m is −2, −1, 0, +1 or +2 and the compound comprises a counterion when m is not 0;

the compound of formula (I) optionally being in the form of a dimer in which two L groups are linked either directly or through a group comprising one or more of $(C_1–C_6)$alkylene, $(C_1–C_6)$alkenylene, arylene, aralkylene, alkarylene, Se, Se—Se, S—S, N=N and C=O or in which L bears two Y groups and two Y' groups;

provided that when $R^2$, $R^3$, $R^5$ and $R^6$ are all H, X is chloro, Y and Y' are both $NH_2$ and L is 1,2-phenylene, $R^1$ is not $CH_3$ when $R^4$ is $CH(CH_3)_2$ and $R^1$ and $R^4$ are not both H.

The compounds of the invention may be in the form of pharmaceutically acceptable salts, solvates and/or prodrugs. Prodrugs are variants of the compounds of the invention which can be converted to compounds of formula (I) in vivo.

The compounds of formula (I) may have one or more chiral centres. When the compounds of formula (I) have one or more chiral centres, they may be in the form of one enantiomer, may be enriched in one enantiomer or may be a racemic mixture.

The term "alkyl" as used herein includes $C_1$ to $C_6$ alkyl groups which may be branched or unbranched and may be open chain or, when they are $C_3$ to $C_6$ groups, cyclic. Unbranched open chain alkyl groups include, for example, methyl, ethyl, propyl, butyl, pentyl and hexyl. Branched open chain alkyl groups include, for example, 2-propyl, 2-butyl and 2-(2-methyl)propyl. Cyclic groups include cyclopropyl, cyclobutyl, cyclopentyl and cyclohexyl. The alkyl groups in the compounds of the invention may optionally be substituted. Substituents include one or more further unsubstituted alkyl groups and/or one or more further substituents, such as, for example, cyano, nitro, $—CO_2(C_1–C_6)$alkyl, halo, thiol (SH), thioether (eg, $S—(C_1–C_6)$alkyl) and sulfonate. The term "alkoxy" means —O-alkyl. The term "alkylthio" means —S-alkyl.

The terms "hydroxy$(C_1–C_6)$alkyl" and "amino$(C_1–C_6)$alkyl" refer to alkyl groups, as defined above, substituted with one or more hydroxyl (OH) or amino ($NH_2$) groups, respectively.

The terms "alkenyl" and "alkynyl" are defined similarly to the term "alkyl" but refer to groups that contain from 2 to 6 carbon atoms and include one or more carbon-carbon double bonds or one or more carbon-carbon triple bonds, respectively. Alkenyl and alkynyl groups may be optionally substituted in the same way as alkyl groups. Examples of alkenyl groups are ethenyl, 1-propenyl, 2-propenyl, 1-butenyl, 2-butenyl, 1,4-butadienyl, cyclohexenyl and cyclohexadienyl.

The term "alkylene" is defined similarly to the definition of the term "alkyl" but includes $C_2$ to $C_6$ groups and represents a divalent species with radicals separated by two or more (eg, from two to six) carbon atoms linked in a chain. Preferably, the alkylene groups are straight chain groups. Examples of alkylene groups are 1,2-ethylene and 1,3-propylene. The terms "alkenylene" and "alkynylene" are defined similarly and refer to divalent radicals containing one or more carbon-carbon double bonds or one or more carbon-carbon triple bonds, respectively.

The term "aryl" as used herein includes aromatic carbocyclic rings such as phenyl, naphthyl and anthracenyl and heterocyclic rings such as pyridyl, imidazolyl, pyrrolyl and furanyl. Aryl groups may optionally be substituted with one or more substituents including, for example, $(C_1–C_6)$alkyl, cyano, nitro, hydroxyl, halo$(C_1–C_6)$alkyl, $—CO_2(C_1–C_6)$alkyl, halo, thiol (SH), thioether (eg, $S—(C_1–C_6)$alkyl) and sulfonate ($SO_3H$). The term "aryloxy" means —O-aryl.

The term "heterocyclic ring" refers to a 3-, 4-, 5-, 6-, -7, or 8- (preferably 5-, 6- or 7-) membered saturated or unsaturated ring, which may be aromatic or non-aromatic, containing from one to three heteroatoms independently selected from N, O and S, eg, indole.

The term "arylene" refers to a divalent radical comprising an aromatic carbocyclic or heterocyclic ring in which the radicals are present at different positions on the ring. An example of an arylene group is 1,2-phenylene.

The term "aralkyl" means alkyl substituted with aryl eg, benzyl. The term "alkaryl" means aryl substituted with alkyl eg, methylphenyl.

The term "aralkylene" refers to a divalent radical that can be derived from an aralkyl group eg, 1-methylene-4-phenyl. Each of the two radicals may be present on the aryl ring or on the alkyl group or one of the radicals may be present on the alkyl group and the other radical present on the aryl ring. The term "alkarylene" is defined similarly.

The term ferrocenylene refers to a diradical derived from ferrocene ($FeCp_2$). Each radical may be present on the same ring or on different rings.

The term "halo" means a halogen radical selected from fluoro, chloro, bromo and iodo. Chloro is particularly preferred. When X is halo in formula (I), it will be appreciated that X may be thought of as having at least some of the character of a negatively charged ion rather than being covalently bonded to the ruthenium atom. Indeed, all ligands X may have some ionic as well as some covalent character.

The term "haloalkyl" means alkyl substituted with one or more halo groups eg, trifluoromethyl.

In the compounds of the invention, $R^1$ and $R^2$ together with the ring to which they are bound in compounds of formula (I) may represent an ortho- or peri-fused carbocyclic or heterocyclic ring system. The carbocyclic and heterocyclic ring systems can be saturated or unsaturated. When the carbocyclic or heterocyclic ring systems are unsaturated, they can be aromatic or non-aromatic. $R^1$ and $R^2$ together with the ring to which they are bound may, for example, represent a wholly carbocyclic fused ring system such as a ring system containing 2 or 3 fused carbocyclic rings eg, optionally substituted, optionally hydrogenated naphthalene or anthracene. Thus, $R^1$ and $R^2$ together with the ring to which they are bound in compounds of formula (I) may represent a fused bicyclic ring such as indan, a fused tricyclic ring such as anthracene or a mono, di, tri, tetra or higher hydrogenated derivative of anthracene. For example, $R^1$ and $R^2$ together with the ring to which they are bound in formula (I) may represent 1,2,3,4-tetrahydronaphthalene, anthracene, 1,4-dihydroanthracene or 1,4,9,10-tetrahydroanthracene.

Preferably, $R^1$, $R^2$, $R^3$, $R^4$, $R^5$ and $R^6$ are independently selected from H, $(C_1-C_6)$alkyl and phenyl or $R^1$ and $R^2$ together with the ring to which they are bound represent indan, anthracene or a hydrogenated derivative of anthracene, said phenyl, indan and anthracene or a hydrogenated derivative of anthracene being optionally substituted by one or more groups independently selected from $(C_1-C_6)$alkyl, $(C_2-C_6)$alkenyl, $(C_2-C_6)$alkynyl, hydroxy$(C_1-C_6)$alkyl, amino$(C_1-C_6)$alkyl, phenyl, benzyl, halo, hydroxyl, carboxyl, $CO_2(C_1-C_6)$alkyl, $CONH_2$, COH, $CO(C_1-C_6)$alkyl, $SO_3H$, $SO_2NH_2$, phenoxy, $(C_1-C_6)$alkylthio, $NH_2$ or $(C_1-C_6)$alkoxy. Most preferably, one of $R^1$, $R^2$, $R^3$, $R^4$, $R^5$ and $R^6$ is phenyl and the other groups are all H, or one or two of $R^1$, $R^2$, $R^3$, $R^4$, $R^5$ and $R^6$ is or are $(C_1-C_6)$alkyl and the other groups are H, or $R^1$ and $R^2$ together with the ring to which they are bound represent anthracene or a hydrogenated derivative of anthracene.

In another embodiment of the invention, one or more of $R^1$ to $R^6$ is or are optionally covalently bonded via a carbon-carbon, carbon-nitrogen or carbon-oxygen bond to another $R^1$ to $R^6$ group on another compound of formula (I). Thus, the compounds of the invention may be multinuclear complexes in which two or more compounds of formula (I) are linked together. Examples of dinuclear complexes include compounds in which the $C_6(R^1R^2R^3R^4R^5R^6)$ group is a group of formula $C_6(R^2R^3R^4R^5R^6)$—$R^1$—$C_6(R^2R^3R^4R^5R^6)$, wherein $R^1$ is $(C_1-C_6)$alkylene optionally comprising one or more groups of formula —O—, $NR^{14}$ and $(NR^{14}R^{15})^+$, wherein $R^{14}$ and $R^{15}$ are as defined above. Also, two or more other groups on the aromatic rings can be linked such that a tricyclic ring is formed, for example in the form of a dibenzo crown ether. Trinuclear complexes include, for example, those compounds in which the $C_6(R^1R^2R^3R^4R^5R^6)$ group is a group of formula $X'(-R^1-(C_6(R^2R^3R^4R^5R^6))_3$, wherein $X'$ is $CR^{14}$, N or $(NR^{14})^+$ and $R^{14}$ is as defined above. Similarly, examples of tetranuclear complexes are those compounds in which the $C_6(R^1R^2R^3R^4R^5R^6)$ group is a group of formula $C(-R^1-(C_6(R^2R^3R^4R^5R^6))_4$.

Compounds of the invention may be charged (either positively or negatively) or uncharged. In formula (I), it is preferred that m is +1. When m is not equal to zero, the compounds of formula (I) comprise a counterion. Suitable counterions include non-nucleophilic ions such as, for example, $PF_6^-$ and $BF_4^-$.

In compounds of formula (I), X is a neutral or negatively charged O-, N- or S-donor ligand or halo. Suitable ligands include, for example, $H_2O$, di$((C_1-C_6)$alkyl$)S(O)$, $(C_1-C_6)$alkyl$CO_2^-$ or di$((C_1-C_6)$alkyl$)C$=O. Other ligands include, for example, N-donor nitrile ligands (eg, compounds of formula $(C_1-C_6)$alkylCN) and N-donor pyridine ligands, optionally substituted at one or more of the carbon rings of the pyridine ring eg, by $(C_1-C_6)$alkyl or halo. Other suitable ligands are $(C_1-C_6)$alkyl primary amines such as methylamine and ethylamine. Preferably, X is halo or $CH_3CN$, most preferably, X is chloro.

Y-L-Y' is a bidentate ligand. Preferably, Y-L-Y' is selected from ligands of formulae (II) to (IV):

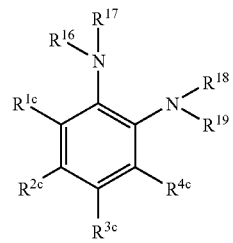

(II)

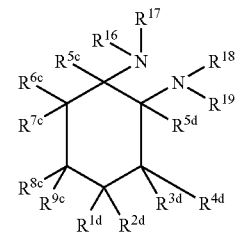

(III)

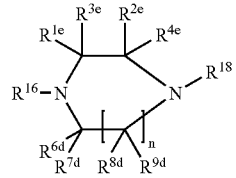

(IV)

wherein: n is 1, 2 or 3, each pair of groups $R^{8d}$ and $R^{9d}$ are the same or different when n is 2 or 3; and $R^{1c}$ to $R^{9c}$, $R^{1d}$ to $R^{9d}$ and $R^{1e}$ to $R^{4e}$, are independently selected from H, $(C_1-C_6)$alkyl, $(C_2-C_6)$alkenyl, $(C_2-C_6)$alkynyl, hydroxy$(C_1-C_6)$alkyl, amino$(C_1-C_6)$alkyl, halo, hydroxy, $CO_2R^{7'}$, $CONR^{8'}R^{9'}$, $COR^{10'}$, $SO_3H$, $SO_2NR^{11'}R^{12'}$, aryloxy, $(C_1-C_6)$alkoxy, $(C_1-C_6)$alkylthio, —N═N—$R^{13'}$, $NR^{14'}R^{15'}$, aryl or aralkyl, and one or more of pairs of groups $R^{1c}$ to $R^{9c}$, $R^{1d}$ to $R^{9d}$ and $R^{1c}$ to $R^{4c}$ that are bonded to the same or adjacent carbon atoms (i.e., carbon atoms that are directly bonded to each other) are optionally covalently bonded to each other to form a saturated or unsaturated carbocyclic or heterocyclic group (the carbocyclic and heterocyclic ring systems can be saturated or unsaturated, and when the carbocyclic or heterocyclic ring systems are unsaturated and bonded to adjacent carbon atoms, they can be aromatic or non-aromatic), and Y-L-Y' is optionally in the form of a dimer in which two compounds of formula (II), two compounds of formula (III) or two compounds of formula (IV) are directly covalently bonded to each other.

The two nitrogen atoms in formulae (II) to (IV) coordinate to the ruthenium atom in formula (I).

It is also preferred that $R^{1c}$ to $R^{9c}$, $R^{1d}$ to $R^{9d}$ and $R^{1e}$ to $R^{4e}$, are independently selected from H, $(C_1-C_6)$alkyl, hydroxy$(C_1-C_6)$alkyl, amino$(C_1-C_6)$alkyl, halo, hydroxyl, $CO_2(C_1-C_6)$alkyl and $(C_1-C_6)$alkoxy.

It is particularly preferred that Y-L-Y' is a ligand of formula (V)

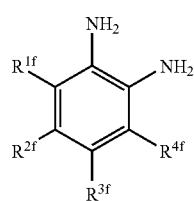

wherein $R^{1f}$, $R^{2f}$, $R^{3f}$ and $R^{4f}$ are independently selected from H, $(C_1-C_6)$alkyl, $(C_2-C_6)$alkenyl, $(C_2-C_6)$alkynyl, hydroxy$(C_1-C_6)$alkyl, amino$(C_1-C_6)$alkyl, halo, hydroxyl, $CO_2R^{7'}$, $CONR^{8'}R^{9'}$, $COR^{10'}$, $SO_3H$, $SO_2NR^{11'}R^{12'}$, aryloxy, $(C_1-C_6)$alkoxy, $(C_1-C_6)$alkylthio, —N=N—$R^{13'}$ and $NR^{14'}R^{15'}$. More preferably, $R^{1f}$, $R^{2f}$, $R^{3f}$ and $R^{4f}$ are independently selected from H, $(C_1-C_6)$alkyl and hydroxyl.

For example, it is preferred that in Y-L-Y' L is 1,2-phenylene, 1,2-cyclohexylene or a $(C_4-C_6)$heterocycle containing two nitrogen atoms (e.g., piperazinyl or homopiperazinyl), optionally substituted with with one or more groups independently selected from $(C_1-C_6)$alkyl, $(C_2-C_6)$alkenyl, $(C_2-C_6)$alkynyl, hydroxy$(C_1-C_6)$alkyl, amino$(C_1-C_6)$alkyl, phenyl, benzyl, halo, hydroxyl, carboxyl, $CO_2(C_1-C_6)$alkyl, $CONH_2$, COH, $CO(C_1-C_6)$alkyl, $SO_3H$, $SO_2NH_2$, phenoxy, $(C_1-C_6)$alkylthio, $NH_2$ or $(C_1-C_6)$alkoxy.

More preferably, in Y-L-Y', $R^{16}$, $R^{17}$, $R^{18}$ and $R^{19}$ are all H. For example, $R^{16}$, $R^{17}$, $R^{18}$ and $R^{19}$ may be H and L is 1,2-phenylene, 1,2-cyclohexylene or homopiperazinyl, optionally substituted with one or two groups selected from $(C_1-C_6)$alkyl and hydroxy.

Another group of ligands Y-L-Y' are those which comprise a fused carbocyclic ring system in which one or more of the $CH_2$ groups of the fused ring system are optionally replaced by C=O groups. Examples of this group of ligands are those in which Y-L-Y' is a ligand of formula (VIA) or (VIB)

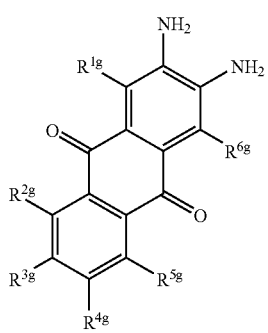

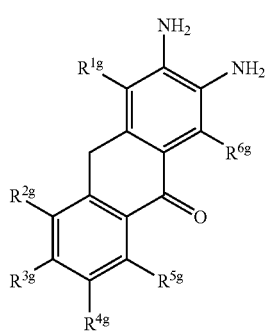

wherein $R^{1g}$, $R^{2g}$, $R^{3g}$, $R^{4g}$, $R^{5g}$ and $R^{6g}$ are independently selected from H, $(C_1-C_6)$alkyl, $(C_2-C_6)$alkenyl, $(C_2-C_6)$alkynyl, hydroxy$(C_1-C_6)$alkyl, amino$(C_1-C_6)$alkyl, halo, hydroxyl, $CO_2R^{7'}$, $CONR^{8'}R^{9'}$, $COR^{10'}$, $SO_3H$, $SO_2NR^{11'}R^{12'}$, aryloxy, $(C_1-C_6)$alkoxy, $(C_1-C_6)$alkylthio, —N=N—$R^{13'}$ and $NR^{14'}R^{15'}$. Preferably, all of $R^{1g}$, $R^{2g}$, $R^{3g}$, $R^{4g}$, $R^{5g}$ and $R^{6g}$ are H. It is also preferred that the ligand is of formula (VIA).

The compounds of formula (I) may be in the form of dimers, which may also be termed dinuclear complexes—such complexes contain two ruthenium atoms. Dinuclear complexes can be provided by employing a ligand which comprises two linked ligands Y-L-Y' so as to bridge between two ruthenium centres. Preferably such linkage is by way of a direct covalent bond between two L groups, so that the ligand has the formula YY'L-LYY'.

Compounds of formula (I) and ligands of formula Y-L-Y' may exist in one or more tautomeric forms, all of which are covered by the present invention.

A particularly preferred group of compounds of formula (I) are those in which: $R^1$, $R^2$, $R^3$, $R^4$, $R^5$ and $R^6$ are independently selected from H, $(C_1-C_6)$alkyl and phenyl or $R^1$ and $R^2$ together with the ring to which they are bound represent indan, anthracene or a hydrogenated derivative of anthracene, said phenyl, indan and anthracene or a hydrogenated derivative of anthracene group being optionally substituted with one or more groups independently selected from $(C_1-C_6)$alkyl, $(C_2-C_6)$alkenyl, $(C_2-C_6)$alkynyl, hydroxy$(C_1-C_6)$alkyl, amino$(C_1-C_6)$alkyl, phenyl, benzyl, halo, hydroxyl, carboxyl, $CO_2(C_1-C_6)$alkyl, $CONH_2$, COH, $CO(C_1-C_6)$alkyl, $SO_3H$, $SO_2NH_2$, phenoxy, $(C_1-C_6)$alkylthio, $NH_2$ or $(C_1-C_6)$alkoxy;

X is chloro;

m is +1;

$R^{16}$, $R^{17}$, $R^{18}$ and $R^{19}$ are all H; and

L is 1,2-phenylene, 1,2-cyclohexylene or a $(C_4-C_6)$heterocycle containing two nitrogen atoms (e.g., piperazinyl or homopiperazinyl), optionally substituted with with one or more groups independently selected from $(C_1-C_6)$alkyl, $(C_2-C_6)$alkenyl, $(C_2-C_6)$alkynyl, hydroxy$(C_1-C_6)$alkyl, amino$(C_1-C_6)$alkyl, phenyl, benzyl, halo, hydroxyl, carboxyl, $CO_2(C_1-C_6)$alkyl, $CONH_2$, COH, $CO(C_1-C_6)$alkyl, $SO_3H$, $SO_2NH_2$, phenoxy, $(C_1-C_6)$alkylthio, $NH_2$ or $(C_1-C_6)$alkoxy.

A further preferred group of compounds of formula (I) is that in which:

one of $R^1$, $R^2$, $R^3$, $R^4$, $R^5$ and $R^6$ is phenyl and the other groups are all H, or one or two of $R^1$, $R^2$, $R^3$, $R^4$, $R^5$ and $R^6$ is or are $(C_1-C_6)$alkyl and the other groups are H, or $R^1$ and $R^2$ together with the ring to which they are bound represent indan, anthracene or a hydrogenated derivative of anthracene;

X is chloro;

m is +1;

$R^{16}$, $R^{17}$, $R^{18}$ and $R^{19}$ are all H; and

L is 1,2-phenylene, 1,2-cyclohexylene or homopiperazinyl, optionally substituted with one or two groups selected from $(C_1-C_6)$alkyl and hydroxy.

The compounds of the invention comprising the complex [(η⁶-biphenyl)Ru(o-phenylenediamine)Cl]⁺, particularly as its salt with the counterion $PF_6^-$, is particularly preferred.

The compounds of the invention have been found to exhibit cytotoxic activity against cancer cell lines and can therefore be expected to show anticancer activity.

In another embodiment, therefore, the present invention provides a compound of formula (I) as defined above without the proviso for use in medicine. The invention also contemplates the provision of a compound of formula (I) as defined above without the proviso for use in the treatment and/or prevention of cancer and the use of a compound of formula (I) as defined above without the provisos in the treatment and/or prevention of cancer.

Also provided by the invention is the use of a compound of formula (I) as defined above without the proviso in the manufacture of a medicament for the treatment and/or prevention of cancer.

Further provided by the invention is a pharmaceutical composition comprising a compound of formula (I) as defined above without the proviso together with one or more pharmaceutically acceptable excipients.

Yet another aspect of the invention is a method of treating and/or preventing cancer which comprises administering to a subject a therapeutically effective amount of a compound of formula (I) as defined above without the proviso or a composition of the invention.

The compounds of the invention may be used directly against a tumour. Alternatively or additionally, the compounds may be used to prevent or inhibit metastasis and/or to kill secondary tumours. It will be understood that the prevention or inhibition of metastasis is encompassed by the term "preventing cancer", as used herein.

The term "tumour" is to be understood as referring to all forms of neoplastic cell growth, including tumours of the lung, liver, blood cells, skin, pancreas, stomach, colon, prostate, uterus, breast, lymph glands and bladder. Ovarian tumours may especially suitable for treatment according to the invention.

Compounds of the invention may be effective in treating and/or preventing tumours caused by cells that are resistant to other cytotoxic drugs, such as cis-platin, for example.

Certain compounds of the invention have the surprising advantage that they exhibit improved non-cross resistance with other anti-cancer agents such as cis-platin and adriamycin whilst still possessing good activity against non-resistant tumour cells. It is clearly highly desirable to be able to kill tumour cells that have developed resistance to other anti-cancer agents.

The compounds of the invention may be administered by a number of routes including, for example, orally, parenterally (eg, by injection intramuscularly, intravenously or subcutaneously), topically, nasally or via slow releasing microcarriers. Thus, suitable excipients for use in the pharmaceutical compositions of the invention include saline, sterile water, creams, ointments, solutions, gels, pastes, emulsions, lotions, oils, solid carriers and aerosols.

The compositions of the invention may be formulated in unit or sub-unit dosage form including, for example, tablets, capsules and lozenges and containers containing the composition in a form suitable for parenteral administration. Preferably, the compositions are in a form that is suitable for injection.

The specific dosage level of the compounds and compositions of the invention will depend upon a number of factors, including the biological activity of the specific compound used and the age, body weight and sex of the subject. It will be appreciated that the subject may be a human or a mammalian animal.

The compounds and compositions of the invention can be administered alone or in combination with other compounds. The other compounds may have a biological activity which complements the activity of the compounds of the invention eg, by enhancing its effect in killing tumours or by reducing any side-effects associated with the compounds of the invention.

In another embodiment, the present invention provides a process for preparing the compound of formula (I) which comprises the reaction of a compound of formula [(η⁶-C₆(R¹)(R²)(R³)(R⁴)(R⁵)(R⁶))RuX₂], optionally in the form of a dimer, with Y-L-Y', in a suitable solvent for the reaction, wherein $R^1, R^2, R^3, R^4, R^5, R^6, X, Y, Y'$ and L are as defined for formula (I) above. Preferably, the process comprises the reaction of a compound of formula [(η⁶-C₆(R¹)(R²)(R³)(R⁴)(R⁵)(R⁶))RuX₂], optionally in the form of a dimer, with Y-L-Y' at a temperature of from 0° C. to 100° C. (eg, 10° C. to 80° C.) in a polar solvent (such as a (C₁–C₄)alkanol, di(C₁–C₆)alkyl ketone (eg, acetone) or water or mixtures thereof). The compound of formula (I) can be separated from the reaction mixture, for example by crystallisation from the reaction mixture following the addition of a counterion for the compound of formula (I) (e.g., $PF_6^-$) in the form of a salt that is soluble in the reaction mixture e.g., $NH_4^+PF_6^-$. The compound is optionally purified (eg, by recrystallisation from a suitable solvent or mixture of two or more different solvents).

Suitable compounds of formula [(η⁶-C₆(R¹)(R²)(R³)(R⁴)(R⁵)(R⁶))RuX₂] for use as starting materials (starting ruthenium complexes) in the process of the invention can be produced as described in WO 01/30790 and WO 02/02572. Compounds of formula Y-L-Y' are either commercially available or can be synthesised by routes well known to those skilled in the art.

The invention will now be described with reference to the following non-limiting examples.

EXAMPLES

Starting Materials

[Ru(η-p-cymene)(CH₃CN)₂Cl]PF₆ was prepared as follows. [Ru(η⁶-p-cymene)Cl₂]₂ (0.50 g, 0.74 mmol) and NH₄PF₆ (0.256 g, 1.6 mmol) was placed in CH₃CN (20 ml) and stirred for 18 hours at ambient temperature. The precipitate was removed by filtration and the solvent removed on the rotary evaporator to give an orange/red oil. Ether was added and trituration gave a yellowish orange solid.

Yield 0.635 g (91%).

The above complex was used as a starting material for Example 6.

Example 1

[(η⁶-Biphenyl)Ru(o-phenylenediamine)Cl]PF₆

The dimer [Ru(Biphenyl)Cl₂]₂ (0.220 g, 0.35 mmol) was suspended in MeOH/H₂O (50 ml/10 ml) and heated under reflux for one hour and cooled to ambient temperature. Diaminobenzene (0.065 g, 0.60 mmol) in MeOH (5 ml) was then added dropwise and the reaction mixture further heated under reflux for 15 min and filtered. To the filtrate NH₄PF₆ (0.122 g, 0.75 mmol) was added and the volume of the filtrate reduced on the rotary evaporator to about 20 ml and kept in the freezer overnight to give a brownish microcrystalline solid. The product was collected by filtration, washed with MeOH and ether and dried in air. It was recrystallised from MeOH.

Yield (0.180 g, 54%)

$^1$H δ (DMSOd$_6$): 8.49 (d, NH, 2H), 7.81 (m, 2H), 7.47 (m, 3H), 7.18–7.15 (m, 4H), 6.46 (d, NH, 2H), 6.28 (m, 2H), 6.00 (m, 1H), 5.86 (m, 2H).

Example 2

{[(η$^6$-Biphenyl)Ru(diaminobenzidine)Cl]PF$_6$}$_2$

The dimer [Ru(Biphenyl)Cl$_2$]$_2$ (0.365 g, 0.55 mmol) was suspended in MeOH (50 ml) and heated under reflux for one hour and cooled to ambient temperature. Diaminobenzidine (0.065 g, 0.107 mmol) in MeOH (10 ml) was then added dropwise and the reaction mixture further heated under reflux for 20 min and filtered. To the filtrate NH$_4$PF$_6$ (0.401 g, 2.45 mmol) was added and the volume of the filtrate reduced on the rotary evaporator to about 20 ml and kept in the freezer overnight to give a brownish microcrystalline solid. The product was collected by filtration, washed with MeOH and ether and dried in air.

Yield (0.435 g, 80%).

$^1$H δ(DMSOd$_6$): 8.42 (m, NH, 4H), 7.86 (m, 4H), 7.5 (m, 6H), 7.36–7.51 (m, 6H), 6.58 (m, NH, 4H), 6.30 (m, 4H), 6.02 (m, 2H), 5.91 (m, 4H).

Example 3

[(η$^6$-dihydroanthracene)Ru(o-phenylenediamine)Cl]PF$_6$

The dimer [Ru(tetrahydroanthracene)Cl$_2$]$_2$ (0.140 g, 0.20 mmol) was suspended in MeOH (40 ml) and water (8 ml) and heated under reflux for one hour and cooled to ambient temperature. 1,2-Diaminobenzene (0.045 g, 0.042 mmol) in MeOH (5 ml) was then added dropwise and the reaction mixture further heated under reflux for 20 min and filtered to give a red solution. To the filtrate NH$_4$PF$_6$ (0.100 g, 0.61 mmol) was added and the solvent was taken off on the rotary evaporator to give a reddish solid. The solid was recrystallised from methanol and was collected by filtration, washed with MeOH and ether and dried in air.

Yield 81 mg, 35% $^1$H δ(DMSOd$_6$): 8.15 (d, NH, 2H), 7.24–7.13 (m, 8H), 6.25 (d, NH, 2H), 5.78–5.73 (m, 4H), 4.11–3.92 (m, 4H).

Example 4

[(η$^6$-Biphenyl)Ru(2,3-diaminophenol)Cl]PF$_6$

The above complex was prepared in the same way as the compound of Example 2.

Yield 38%

$^1$H δ(DMSOd$_6$): 8.30 (d, NH, 1H), 8.04 (d, NH, 1H), 7.82 (m, 2H), 7.49 (m, 3H) 6.98 (m, 1H), 6.65 (m, 2H), 6.43 (d, NH, 1H), 6.24 (m, 2H), 6.01–5.94 (m, 3H), 5.46 (m, NH, 1H).

Example 5

[(η$^6$-indan)Ru(3,4-diaminotoluene)Cl]PF$_6$

The dimer [Ru(C$_9$H$_{10}$)Cl$_2$]$_2$, ([Ru(indan)Cl$_2$]$_2$) (0.244 g, 0.42 mmol) was dissolved in MeOH (25 ml) and 3,4-diaminotoluene (0.100 g, 0.84 mmol) in MeOH (5 ml) was added and stirred at ambient temperature for two hours. It was filtered and to the filtrate NH$_4$PF$_6$ (0.205 g, 1.26 mmol) was added and the volume of the filtrate reduced on the rotary evaporator to about 3 ml and kept in the freezer overnight to give a brownish microcrystalline solid. The product was collected by filtration, washed with MeOH and ether and dried in air. It was recrystallised from MeOH.

Yield 79%

$^1$H δ(DMSOd$_6$): 8.04 (m, NH, 2H), 7.08 (m, 1H), 6.98 (m, 2H), 6.21 (m, NH, 2H), 5.73 (m, 2H), 5.63 (m, 2H), 2.25 (s, 3H), 2.74–2.68 (m, 4H), 2.09–1.9 (m, 2H).

Example 6

[(η$^6$-p-cymene)Ru(o-phenylenediamine)Cl]PF$_6$

[Ru(η-p-cymene)(CH$_3$CN)$_2$Cl]PF$_6$ (0.12 g 0.25 mmol) was dissolved in CH$_3$CN (20 ml) to give a yellowish solution. To this 1,2 phenylenediamine (0.151 g, 1.40 mmol) was added and the reaction mixture stirred at ambient temperature for 18 hours to give a deep red solution. The solvent was removed on the rotary evaporator to give a brownish/red oily solid. This was washed many times with ether and triturated to give a reddish powder. Yield 47%.

$^1$H δ(DMSOd$_6$): 8.58 (d, NH, 2H), 7.20–7.23 (m, 4H), 6.21 (d, NH, 2H), 5.85 (d, 2H), 5.65 (d, 2H), 3.06 (s, 1H), 2.26 (s, 3H), 1.23 (d, 6H).

Example 7

[(η$^6$-1,2,3,4-tetrahydronaphthalene)Ru(1,2-diamino-4-nitrobenzene)Cl]PF$_6$

To [Ru(C$_{10}$H$_{12}$)Cl$_2$]$_2$ (0.154 g, 0.253 mM) in MeOH (30 ml), 1,2 diamino-3-nitro benzene (0.078 g, 0.51 mM) suspended in MeOH (5 ml) was added and the reaction mixture stirred at ambient temperature for 2.5 hours to give a clear dark red solution. The solution was filtered and the volume of the filtrate was reduced on the rotary evaporator to about 7 ml. NH$_4$PF$_6$ (0.2 g, 1.2 mM) was added and the flask left at −20° C. for two days. Dark/black solid (0.55 g) was collected by filtration.

NMR (DMSOd$_6$) 1.93 (m, 2H), 2.60 (m, 2H), 2.75 (m, 2H), 5.0 (s, NH$_2$), 5.52 (m, 2H), 5.74 (m, 2H), 6.52 (s, 1H), 7.38 (m, 2H).

Example 8

[(η$^6$-indan)Ru(1,2-diaminoanthraquinone)Cl]Cl

To [Ru(C$_9$H$_{10}$)Cl$_2$] (0.170 g, 0.3 mM) in MeOH (40 ml), 1,2-diaminoanthraquinone 0.143 g, 0.6 mM) was added and the reaction mixture stirred at ambient temperature for 2 h. After this time a reddish/violet solid precipitated out of solution. The precipitate was collected by filtration and dried in air. Yield 0.23 g, 75%.

NMR (DMSOd$_6$) 1.93 (m, 2H), 2.60 (m, 2H), 2.75 (m, 2H), 5.77 (m, 2H), 5.88 (m, 2H), 6.30 (s, 2H, NH$_2$), 6.70 (d, 1H), 7.47 (d, 1H), 7.80 (m, 2H), 7.90 (s, 2H, NH$_2$), 8.10 (m, 1H), 8.20 (m, 1H).

Example 9

[(η⁶-1,2,3,4-tetrahydronaphthalene)Ru(1,2-diaminoanthraquinone)Cl]Cl

The compound of Example 9 was prepared in an analogous way to the compound of Example 8. Yield (70%). NMR (DMSOd$_6$) 1.66–1.73 (m, 4H), 2.42–2.45 (m, 2H), 2.74–2.77 (m, 2H), 5.54 (m, 2H), 5.73 (m, 2H), 6.33 (s, 2H, NH$_2$), 6.77 (d, 1H), 7.47 (d, 1H), 7.80 (m, 2H), 7.92 (s, 2H, NH$_2$), 8.10 (m, 1H), 8.20 (m, 1H).

B. Biological Data

1. Protocol for Testing Ru Compounds

The human ovarian cells were added at a density of 1×10⁴ cells per well to 24-well tissue culture trays (Falcon Plastic, Becton Dickenson, Lincon Park, N.J., USA) and allowed to grow for 72 h before addition of the Ru(II) arene complexes. Stock solutions of the ruthenium compounds were made up fresh in deionised water and sonicated to ensure complete dissolution. These stock solutions were diluted with media to give final concentrations ranging between 0.1 and 100 μM. All compounds were evaluated at each concentration in duplicate wells, and complete assays were repeated a minimum of three times. Cisplatin or carboplatin was employed as a positive and comparative control in each experiment. After 24-hours exposure the drug-containing medium was removed, the cells washed with phosphate buffered saline (PBS) and fresh medium was added. Cell number was assessed after a further 72 h growth using a Coulter counter (Coulter Electronics Ltd, Luton, UK) and the IC$_{50}$ values (concentration of drug causing 50% growth inhibition) calculated by linear regression analysis comparing the inhibitory effects of the drugs against the growth of untreated cells.

The cell lines and methods used are also described in Aird et al, *Br. J. Cancer*, (2002), 86, 1652–1657.

2. Results

Using the above protocol, a number of compounds of the invention were tested on A2780 ovarian cancer cell line, on an A2780 ovarian cancer cell line resistant to cis-platin (A2780$^{CIS}$), and on an A2780 ovarian cancer cell line resistant to adriamycin (A2780$^{AD}$). Some of the compounds were tested on an A549 cell line. The results are shown in Table 1:

Table 1 is a summary of cytotoxicity data for different cell types

| Example | Schematic structure | A2780 IC$_{50}$ (μM) | A2780$^{CIS}$ Fold resistance | A2780$^{AD}$ fold resistance |
|---|---|---|---|---|
| EX 1 | 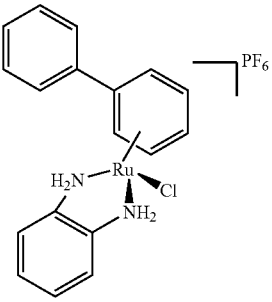 | 5 | 1 | 0.8 |
| EX 2 | 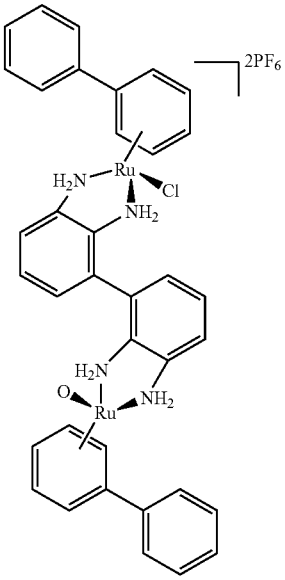 | 52 | | |

-continued
| Example | Schematic Structure | | | |
|---|---|---|---|---|
| EX 3 | 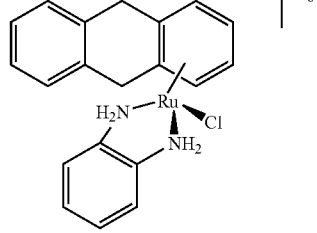 | 7 | 5 | 2 |
| EX 4 | 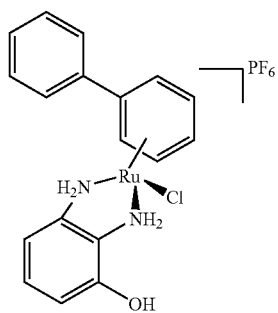 | 32 | | |
| EX 5 | 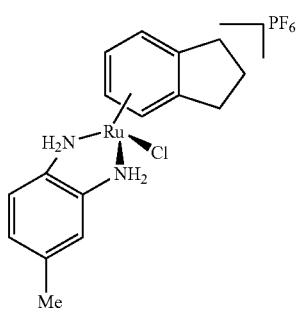 | 4 | | |
| EX 6 | 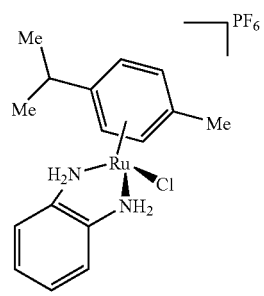 | 11 | 1 | 0.6 |
| Example | Schematic Structure | A2780 IC$_{50}$ (μM) | A549 IC$_{50}$ (μM) |
|---|---|---|---|
| Example 7 | 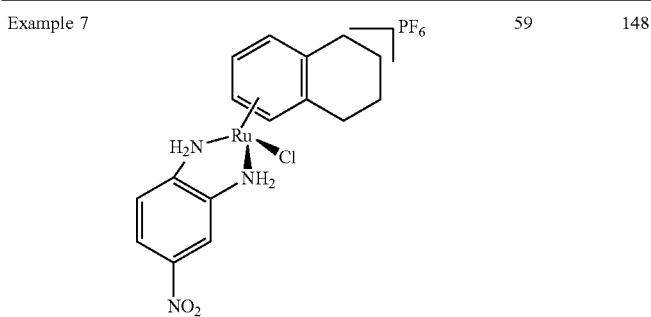 | 59 | 148 |

Example 8

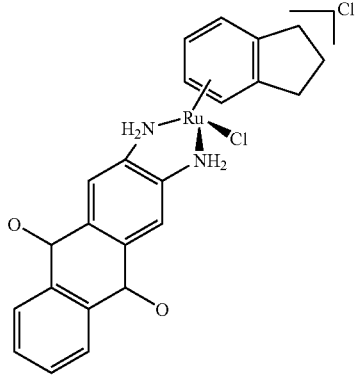

15    48

Example 9

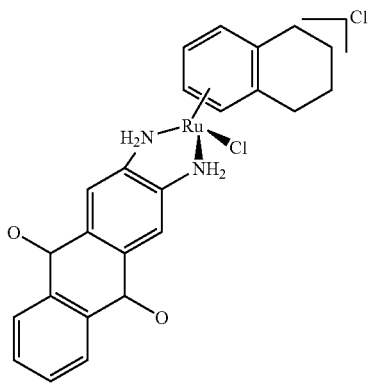

37    61

Data were obtained showing cytotoxicity for the analogues of the compounds of Examples 1, 3 and 6 in which the 1,2-diaminobenzene ligand is replaced by a 1,2-diaminoethane ligand (comparative Examples 1, 2 and 3, respectively) in an otherwise identical molecule. The results are as follows:

| Example | A2780 IC$_{50}$(μM) | A2780$^{CIS}$ Fold resistance | A2780$^{AD}$ fold resistance |
| --- | --- | --- | --- |
| EX 1 | 5 | 1 | 0.8 |
| Comparative Example 1 | 5 | 1 | 45 |
| EX 3 | 7 | 5 | 2 |
| Comparative Example 2 | 2 | 0.5 | >100 |
| EX 6 | 11 | 1 | 0.6 |
| Comparative Example 3 | 10 | 0.6 | 10 |

The invention claimed is:

1. Ruthenium(II) compound of formula (I):

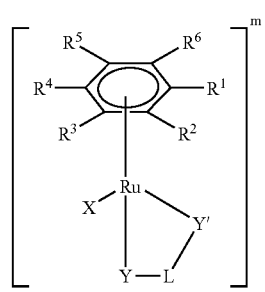

(I)

wherein: $R^1$, $R^2$, $R^3$, $R^4$, $R^5$ and $R^6$ independently represent H, (C$_1$–C$_6$)alkyl, (C$_2$–C$_6$)alkenyl, (C$_2$–C$_6$)alkynyl, hydroxy(C$_1$–C$_6$)alkyl, amino(C$_1$–C$_6$)alkyl, halo, hydroxyl, CO$_2$R$^7$, CONR$^8$R$^9$, COR$^{10}$, SO$_3$H, SO$_2$NR$^{11}$R$^{12}$, aryloxy, (C$_1$–C$_6$)alkoxy, (C$_1$–C$_6$)alkythio, —N═N—R$^{13}$, NR$^{14}$R$^{15}$, aryl or aralkyl, which latter two groups are optionally substituted on the aromatic ring by one or more groups independently selected from (C$_1$–C$_6$)alkyl, (C$_2$–C$_6$)alkenyl, (C$_2$–C$_6$)

alkynyl, hydroxy($C_1$–$C_6$)alkyl, amino($C_1$–$C_6$)alkyl, aryl, aralkyl, halo, hydroxyl, $CO_2R^{7a}$, $CONR^{8a}R^{9a}$, $COR^{10a}$, $SO_3G$, $SO_2NR^{11a}R^{12a}$, aryloxy, ($C_1$–$C_6$) alkoxy, ($C_1$–$C_6$)alkylthio, —N=N—$R^{13a}$, $NR^{14a}R^{15a}$, or $R^1$ and $R^2$ together with the ring to which they are bound represent a saturated or unsaturated carbocyclic or heterocyclic group containing up to three 3- to 8-membered carbocyclic or heterocyclic rings, wherein each carbocyclic or heterocyclic ring may be fused to one or more other carbocyclic or heterocyclic rings, and wherein each of the rings may be optionally substituted by one or more groups independently selected from ($C_1$–$C_6$)alkyl, ($C_2$–$C_6$)alkenyl, ($C_2$–$C_6$)alkynyl, hydroxy($C_1$–$C_6$)alkyl, amino($C_1$–$C_6$)alkyl, aryl, aralkyl, halo, hydroxyl, $CO_2R^{7b}$, $CONR^{8b}R^{9b}$, $COR^{10b}$, $SO_3G'$, $SO_2NR^{11b}R^{12b}$, aryloxy, ($C_1$–$C_6$)alkylthio, —N=N—$R^{13b}$, $NR^{14b}R^{15b}$ or ($C_1$–$C_6$)alkoxy;

one or more of $R^1$ to $R^6$ optionally being covalently bonded via a carbon-carbon, carbon-nitrogen or carbon-oxygen bond to another $R^1$ to $R^6$ group on another compound of formula (I);

$R^7$, $R^8$, $R^9$, $R^{10}$, $R^{11}$, $R^{12}$, $R^{13}$, $R^{14}$, $R^{15}$, $R^{7a}$, $R^{8a}$, $R^{9a}$, $R^{10a}$, $R^{11a}$, $R^{12a}$, $R^{13a}$, $R^{14a}$, $R^{15a}$, $R^{7b}$, $R^{8b}$, $R^{9b}$, $R^{10b}$, $R^{11b}$, $R^{12b}$, $R^{13b}$, $R^{14b}$ and $R^{15b}$ are independently selected from H, ($C_1$–$C_6$)alkyl, aryl, or aralkyl;

X is a neutral or negatively charged O-, N- or S-donor ligand or halo;

G and G' are independently selected from alkali metals, aryl, aralkyl and ($C_1$–$C_6$) alkyl;

Y is $NR^{16}R^{17}$ and Y' is $NR^{18}R^{19}$, wherein $R^{16}$, $R^{17}$, $R^{18}$ and $R^{19}$ are independently selected from H, ($C_1$–$C_6$) alkyl, aryl or aralkyl;

L is 1,2-arylene, 1,2-($C_5$–$C_8$)cycloalkylene or ($C_2$–$C_6$) alkylene, provided that when L is ($C_2$–$C_6$)alkylene, one of $R^{16}$ and $R^{17}$ is covalently bonded to one of $R^{18}$ and $R^{19}$ such that they form with L a ring containing Y and Y', said 1,2-arylene, 1,2-($C_5$–$C_8$)cycloalkylene and ($C_2$–$C_6$)alkylene groups being optionally fused with one or more saturated or unsaturated carbocyclic or heterocyclic groups containing up to three 3- to 8-membered carbocyclic or heterocyclic rings, wherein each carbocyclic or heterocyclic ring may be fused to one or more other carbocyclic or heterocyclic rings, said 1,2-arylene, 1,2-($C_5$–$C_8$)cycloalkylene and ($C_2$–$C_6$)alkylene groups and/or the groups to which they are fused being optionally substituted with one or more groups independently selected from ($C_1$–$C_6$)alkyl, ($C_2$–$C_6$) alkenyl, ($C_2$–$C_6$)alkynyl, hydroxy($C_1$–$C_6$)alkyl, amino ($C_1$–$C_6$)alkyl, halo, hydroxyl, nitro, $CO_2R^{7'}$, $CONR^{8'}R^{9'}$, $COR^{10'}$, $SO_3H$, $SO_2N R^{11'}R^{12'}$, aryloxy, ($C_1$–$C_6$)alkoxy, ($C_1$–$C_6$)alkylthio, —N=N—$R^{13'}$, $NR^{14'}R^{15'}$, aryl or aralkyl, and having one or more $CH_2$ groups optionally replaced by C=O groups, wherein $R^{7'}$, $R^{8'}$, $R^{9'}$, $R^{10'}$, $R^{11'}$, $R^{12'}$, $R^{13'}$, $R^{14'}$ and $R^{15'}$ are independently selected from H, ($C_1$–$C_6$)alkyl, aryl or aralkyl;

m is −2, −1, 0, +1 or +2 and the compound comprises a counterion when m is not 0;

the compound of formula (I) optionally being in the form of a dimer in which two L groups are linked either directly or through a group comprising one or more of ($C_1$–$C_6$)alkylene, ($C_1$–$C_6$)alkenylene, arylene, aralkylene, alkarylene, Se, Se—Se, S—S, N=N and C=O or in which L bears two Y groups and two Y' groups;

provided that when $R^2$, $R^3$, $R^5$ and $R^6$ are all H, X is chloro, Y and Y' are both $NH_2$ and L is 1,2-phenylene, $R^1$ is not $CH_3$ when $R^4$ is $CH(CH_3)_2$ and $R^1$ and $R^4$ are not both H.

2. Compound as claimed in claim 1, wherein $R^1$, $R^2$, $R^3$, $R^4$, $R^5$ and $R^6$ are independently selected from H, ($C_1$–$C_6$) alkyl and phenyl or $R^1$ and $R^2$ together with the ring to which they are bound represent indan, anthracene or a hydrogenated derivative of anthracene, said phenyl, indan and anthracene or a hydrogenated derivative of anthracene group being optionally substituted by one or more groups independently selected from ($C_1$–$C_6$)alkyl, ($C_2$–$C_6$)alkenyl, ($C_2$–$C_6$)alkynyl, hydroxy($C_1$–$C_6$)alkyl, amino($C_1$–$C_6$)alkyl, phenyl, benzyl, halo, hydroxyl, carboxyl, $CO_2$($C_1$–$C_6$)alkyl, $CONH_2$, COH, CO($C_1$–$C_6$)alkyl, $SO_3H$, $SO_2NH_2$, phenoxy, ($C_1$–$C_6$)alkylthio, $NH_2$ or ($C_1$–$C_6$)alkoxy.

3. Compound as claimed in claim 1, wherein m is +1.

4. Compound as claimed in claim 1, wherein X is halo.

5. Compound as claimed in claim 1, wherein Y-L-Y' is selected from ligands of formulae (II) to (IV):

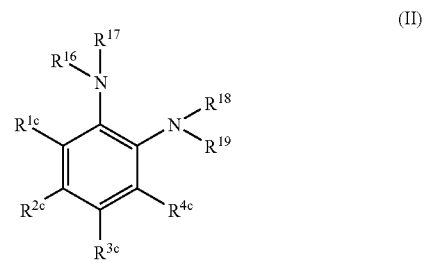

(II)

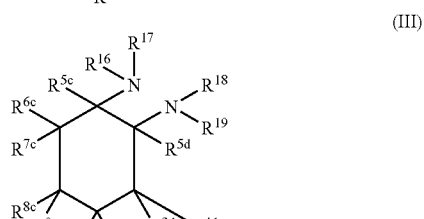

(III)

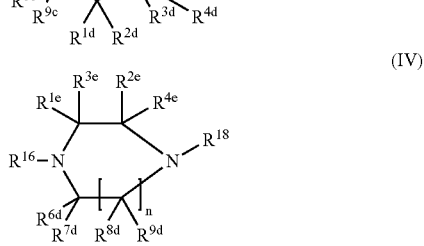

(IV)

wherein: n is 1, 2 or 3, each pair of groups $R^{8d}$ and $R^{9d}$ are the same or different when n is 2 or 3; and $R^{1c}$ to $R^{9c}$, $R^{1d}$ to $R^{9d}$ and $R^{1e}$ to $R^{4e}$, are independently selected from H, ($C_1$–$C_6$)alkyl, ($C_2$–$C_6$)alkenyl, ($C_2$–$C_6$)alkynyl, hydroxy($C_1$–$C_6$)alkyl, amino($C_1$–$C_6$) alkyl, halo, hydroxyl, $CO_2R^{7'}$, $CONR^{8'}R^{9'}$, $COR^{10'}$, $SO_3H$, $SO_2N R^{11'}R^{12'}$, aryloxy, ($C_1$–$C_6$)alkoxy, ($C_1$–$C_6$)alkylthio, —N=N—$R^{13'}$, $NR^{14'}R^{15'}$, aryl or aralkyl, and one or more of pairs of groups $R^{1c}$ to $R^{9c}$, $R^{1d}$ to $R^{9d}$ and $R^{1e}$ to $R^{4e}$ that are bonded to the same or adjacent carbon atoms are optionally covalently bonded to each other to form a saturated or unsaturated carbocyclic or heterocyclic group, and Y-L-Y' is optionally in the form of a dimer in which two compounds of formula (II), two compounds of formula (III) or two compounds of formula (IV) are directly covalently bonded to each other.

6. Compound as claimed in claim 5, wherein $R^{16}$, $R^{17}$, $R^{18}$ and $R^{19}$ are all H.

7. Compound as claimed in claim 5, wherein $R^{1c}$ to $R^{9c}$, $R^{1d}$ to $R^{9d}$ and $R^{1e}$ to $R^{4e}$, are independently selected from H, $(C_1-C_6)$alkyl, hydroxy$(C_1-C_6)$alkyl, amino$(C_1-C_6)$alkyl, halo, hydroxyl, $CO_2(C_1-C_6)$alkyl and $(C_1-C_6)$alkoxy.

8. Compound as claimed in claim 5, wherein Y-L-Y' is a ligand of formula (V)

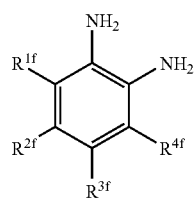

(V)

wherein $R^{1f}$, $R^{2f}$, $R^{3f}$ and $R^{4f}$ are independently selected from H, $(C_1-C_6)$alkyl, $(C_2-C_6)$alkenyl, $(C_2-C_6)$alkynyl, hydroxy$(C_1-C_6)$alkyl, amino$(C_1-C_6)$alkyl, halo, hydroxyl, $CO_2R^{7'}$, $CONR^{8'}R^{9'}$, $COR^{10'}$, $SO_3H$, $SO_2NR^{11'}R^{12'}$, aryloxy, $(C_1-C_6)$alkoxy, $(C_1-C_6)$alkylthio, $-N=N-R^{13'}$ and $NR^{14'}R^{15'}$.

9. Compound as claimed in claim 5, wherein Y-L-Y' is a ligand of formula (VIA) or (VIB)

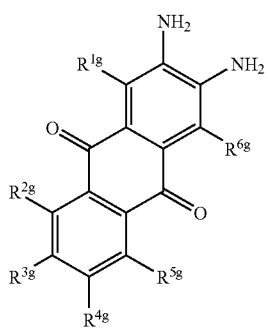

(VIA)

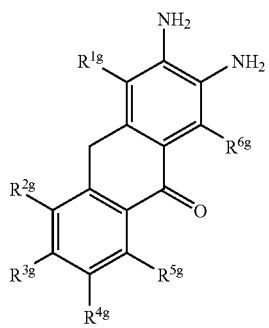

(VIB)

wherein $R^{1g}$, $R^{2g}$, $R^{3g}$, $R^{4g}$, $R^{5g}$ and $R^{6g}$ are independently selected from H, $(C_1-C_6)$alkyl, $(C_2-C_6)$alkenyl, $(C_2-C_6)$alkynyl, hydroxy$(C_1-C_6)$alkyl, amino$(C_1-C_6)$alkyl, halo, hydroxyl, $CO_2R^{7'}$, $CONR^{8'}R^{9'}$, $COR^{10'}$, $SO_3H$, $SO_2NR^{11'}R^{12'}$, aryloxy, $(C_1-C_6)$alkoxy, $(C_1-C_6)$alkylthio, $-N=N-R^{13'}$ and $NR^{14'}R^{15'}$.

10. Compound as claimed in claim 8, wherein $R^{1f}$, $R^{2f}$, $R^{3f}$ and $R^{4f}$ are independently selected from H, $(C_1-C_6)$alkyl and hydroxyl.

11. Compound as claimed in claim 9, wherein $R^{1g}$, $R^{2g}$, $R^{3g}$, $R^{4g}$, $R^{5g}$ and $R^{6g}$ are all H.

12. Pharmaceutical composition comprising a compound of formula (I):

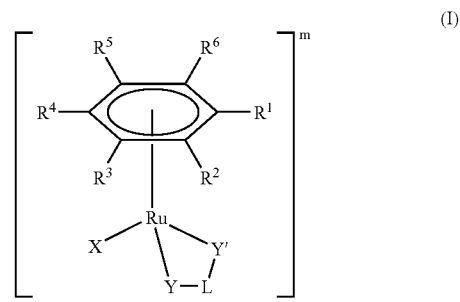

(I)

wherein: $R^1$, $R^2$, $R^3$, $R^4$, $R^5$ and $R^6$ independently represent H, $(C_1-C_6)$alkyl, $(C_2-C_6)$alkenyl, $(C_2-C_6)$alkynyl, hydroxy$(C_1-C_6)$alkyl, amino$(C_1-C_6)$alkyl, halo, hydroxyl, $CO_2R^7$, $CONR^8R^9$, $COR^{10}$, $SO_3H$, $SO_2NR^{11}R^{12}$, aryloxy, $(C_1-C_6)$alkoxy, $(C_1-C_6)$alkylthio, $-N=N-R^{13}$, $NR^{14}R^{15}$, aryl or aralkyl, which latter two groups are optionally substituted on the aromatic ring by one or more groups independently selected from $(C_1-C_6)$alkyl, $(C_2-C_6)$alkenyl, $(C_2-C_6)$alkynyl, hydroxy$(C_1-C_6)$alkyl, amino$(C_1-C_6)$alkyl, aryl, aralkyl, halo, hydroxyl, $CO_2R^{7a}$, $CONR^{8a}R^{9a}$, $COR^{10a}$, $SO_3G$, $SO_2NR^{11a}R^{12a}$, aryloxy, $(C_1-C_6)$alkoxy, $(C_1-C_6)$alkylthio, $-N=N-R^{13a}$, $NR^{14a}R^{15a}$, or $R^1$ and $R^2$ together with the ring to which they are bound represent a saturated or unsaturated carbocyclic or heterocyclic group containing up to three 3- to 8-membered carbocyclic or heterocyclic rings, wherein each carbocyclic or heterocyclic ring may be fused to one or more other carbocyclic or heterocyclic rings, and wherein each of the rings may be optionally substituted by one or more groups independently selected from $(C_1-C_6)$alkyl, $(C_2-C_6)$alkenyl, $(C_2-C_6)$alkynyl, hydroxy$(C_1-C_6)$alkyl, amino$(C_1-C_6)$alkyl, aryl, aralkyl, halo, hydroxyl, $CO_2R^{7b}$, $CONR^{8b}R^{9b}$, $COR^{10b}$, $SO_3G'$, $SO_2NR^{11b}R^{12b}$, aryloxy, $(C_1-C_6)$alkylthio, $-N=N-R^{13b}$, $NR^{14b}R^{15b}$ or $(C_1-C_6)$alkoxy;

one or more of $R^1$ to $R^6$ optionally being covalently bonded via a carbon-carbon, carbon-nitrogen or carbon-oxygen bond to another $R^1$ to $R^6$ group on another compound of formula (I);

$R^7$, $R^8$, $R^9$, $R^{10}$, $R^{11}$, $R^{12}$, $R^{13}$, $R^{14}$, $R^{15}$, $R^{7a}$, $R^{8a}$, $R^{9a}$, $R^{10a}$, $R^{11a}$, $R^{12a}$, $R^{13a}$, $R^{14a}$, $R^{15a}$, $R^{7b}$, $R^{8b}$, $R^{9b}$, $R^{10b}$, $R^{11b}$, $R^{12b}$, $R^{13b}$, $R^{14b}$ and $R^{15b}$ are independently selected from H, $(C_1-C_6)$alkyl, aryl or aralkyl;

X is a neutral or negatively charged O-, N- or S-donor ligand or halo;

G and G' are independently selected from alkali metals, aryl, aralkyl and $(C_1-C_6)$ alkyl;

Y is $NR^{16}R^{17}$ and Y' is $NR^{18}R^{19}$, wherein $R^{16}$, $R^{17}$, $R^{18}$ and $R^{19}$ are independently selected from H, $(C_1-C_6)$ alkyl, aryl or aralkyl;

L is 1,2-arylene, 1,2-$(C_5-C_8)$cycloalkylene or $(C_2-C_6)$ alkylene, provided that when L is $(C_2-C_6)$alkylene, one of $R^{16}$ and $R^{17}$ is covalently bonded to one of $R^{18}$ and $R^{19}$ such that they form with L a ring containing Y and Y', said 1,2-arylene, 1,2-$(C_5-C_8)$cycloalkylene and $(C_2-C_6)$alkylene groups being optionally fused with one or more saturated or unsaturated carbocyclic or heterocyclic groups containing up to three 3- to 8-membered carbocyclic or heterocyclic rings, wherein each carbocyclic or heterocyclic ring may be fused to one or more other carbocyclic or heterocyclic rings, said 1,2-arylene, 1,2-($C_5$–$C_8$)cycloalkylene and ($C_2$–$C_6$)alkylene groups and/or the groups to which they are fused being optionally substituted with one or more groups independently selected from ($C_1$–$C_6$)alkyl, ($C_2$–$C_6$)alkenyl, ($C_2$–$C_6$)alkynyl, hydroxy($C_1$–$C_6$)alkyl, amino($C_1$–$C_6$)alkyl, halo, hydroxyl, nitro, $CO_2R^{7'}$, $CONR^{8'}R^{9'}$, $COR^{10'}$, $SO_3H$, $SO_2NR^{11'}R^{12'}$, aryloxy, ($C_1$–$C_6$)alkoxy, ($C_1$–$C_6$)alkylthio, —N=N—$R^{13'}$, $NR^{14'}R^{15'}$, aryl or aralkyl, and having one or more $CH_2$ groups optionally replaced by C=O groups, wherein $R^{7'}$, $R^{8'}$, $R^{9'}$, $R^{10'}$, $R^{11'}$, $R^{12'}$, $R^{13'}$, $R^{14'}$ and $R^{15'}$ are independently selected from H, ($C_1$–$C_6$)alkyl, aryl, or aralkyl;

m is −2, −1, 0, +1 or +2 and the compound comprises a counterion when m is not 0;

the compound of formula (I) optionally being in the form of a dimer in which two L groups are linked either directly or through a group comprising one or more of ($C_1$–$C_6$)alkylene, ($C_1$–$C_6$)alkenylene, arylene, aralkylene, alkarylene, Se, Se—Se, S—S, N=N and C=O or in which L bears two Y groups and two Y' groups, together with one or more pharmaceutically acceptable excipients.

13. A method of treating cancer which comprises administering to a subject a therapeutically effective amount of a compound of formula (I):

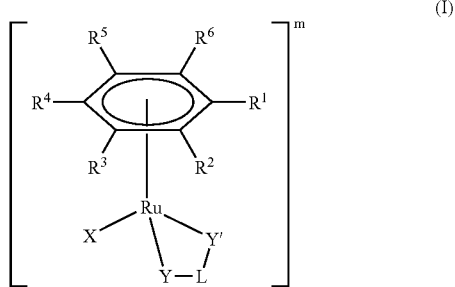

(I)

wherein: $R^1$, $R^2$, $R^3$, $R^4$, $R^5$ and $R^6$ independently represent H, ($C_1$–$C_6$)alkyl, ($C_2$–$C_6$)alkenyl, ($C_2$–$C_6$)alkynyl, hydroxy($C_1$–$C_6$)alkyl, amino($C_1$–$C_6$)alkyl, halo, hydroxyl, $CO_2R^7$, $CONR^8R^9$, $COR^{10}$, $SO_3H$, $SO_2NR^{11}R^{12}$, aryloxy, ($C_1$–$C_6$)alkoxy, ($C_1$–$C_6$)alkylthio, —N=N—$R^{13}$, $NR^{14}R^{15}$, aryl or aralkyl, which latter two groups are optionally substituted on the aromatic ring by one or more groups independently selected from ($C_1$–$C_6$)alkyl, ($C_2$–$C_6$)alkenyl, ($C_2$–$C_6$)alkynyl, hydroxy($C_1$–$C_6$)alkyl, amino($C_1$–$C_6$)alkyl, aryl, aralkyl, halo, hydroxyl, $CO_2R^{7a}$, $CONR^{8a}R^{9a}$, $COR^{10a}$, $SO_3G$, $SO_2NR^{11a}R^{12a}$, aryloxy ($C_1$–$C_6$)alkoxy, ($C_1$–$C_6$)alkylthio, —N=N—$R^{13a}$, $NR^{14a}R^{15a}$, or $R^1$ and $R^2$ together with the ring to which they are bound represent a saturated or unsaturated carbocyclic or heterocyclic group containing up to three 3- to 8-membered carbocyclic or heterocyclic rings, wherein each carbocyclic or heterocyclic ring may be fused to one or more other carbocyclic or heterocyclic rings, and wherein each of the rings may be optionally substituted by one or more groups independently selected from ($C_1$–$C_6$)alkyl, ($C_2$–$C_6$)alkenyl, ($C_2$–$C_6$)alkynyl, hydroxy($C_1$–$C_6$)alkyl, amino($C_1$–$C_6$)alkyl, aryl, aralkyl, halo, hydroxyl, $CO_2R^{7b}$, $CONR^{8b}R^{9b}$, $COR^{10b}$, $SO_3G'$, $SO_2NR^{11b}R^{12b}$, aryloxy, ($C_1$–$C_6$)alkylthio, —N=N—$R^{13b}$, $NR^{14b}R^{15b}$ or ($C_1$–$C_6$)alkoxy;

one or more of $R^1$ to $R^6$ optionally being covalently bonded via a carbon-carbon, carbon-nitrogen or carbon-oxygen bond to another $R^1$ to $R^6$ group on another compound of formula (I);

$R^7$, $R^8$, $R^9$, $R^{10}$, $R^{11}$, $R^{12}$, $R^{13}$, $R^{14}$, $R^{15}$, $R^{7a}$, $R^{8a}$, $R^{9a}$, $R^{10a}$, $R^{11a}$, $R^{12a}$, $R^{13a}$, $R^{14a}$, $R^{15a}$, $R^{7b}$, $R^{8b}$, $R^{9b}$, $R^{10b}$, $R^{11b}$, $R^{12b}$, $R^{13b}$, $R^{14b}$ and $R^{15b}$ are independently selected from H, ($C_1$–$C_6$)alkyl, aryl or aralkyl;

X is a neutral or negatively charged O-, N- or S-donor ligand or halo;

G and G' are independently selected from alkali metals, aryl, aralkyl and ($C_1$–$C_6$) alkyl;

Y is $NR^{16}R^{17}$ and Y' is $NR^{18}R^{19}$, wherein $R^{16}$, $R^{17}$, $R^{18}$ and $R^{19}$ are independently selected from H, ($C_1$–$C_6$) alkyl, aryl or aralkyl;

L is 1,2-arylene, 1,2-($C_5$–$C_8$)cycloalkylene or ($C_2$–$C_6$) alkylene, provided that when L is ($C_2$–$C_6$)alkylene, one of $R^{16}$ and $R^{17}$ is covalently bonded to one of $R^{18}$ and $R^{19}$ such that they form with L a ring containing Y and Y', said 1,2-arylene, 1,2-($C_5$–$C_8$)cycloalkylene and ($C_2$–$C_6$)alkylene groups being optionally fused with one or more saturated or unsaturated carbocyclic or heterocyclic groups containing up to three 3- to 8-membered carbocyclic or heterocyclic rings, wherein each carbocyclic or heterocyclic ring may be fused to one or more other carbocyclic or heterocyclic rings, said 1,2-arylene, 1,2-($C_5$–$C_8$)cycloalkylene and ($C_2$–$C_6$)alkylene groups and/or the groups to which they are fused being optionally substituted with one or more groups independently selected from ($C_1$–$C_6$)alkyl, ($C_2$–$C_6$) alkenyl, ($C_2$–$C_6$)alkynyl, hydroxy($C_1$–$C_6$)alkyl, amino($C_1$–$C_6$)alkyl, halo, hydroxyl, nitro, $CO_2R^{7'}$, $CONR^{8'}R^{9'}$, $COR^{10'}$, $SO_3H$, $SO_2NR^{11'}R^{12'}$, aryloxy, ($C_1$–$C_6$)alkoxy, ($C_1$–$C_6$)alkylthio, —N=N—$R^{13'}$, $NR^{14'}R^{15'}$, aryl or aralkyl, and having one or more $CH_2$ groups optionally replaced by C=O groups, wherein $R^{7'}$, $R^{8'}$, $R^{9'}$, $R^{10'}$, $R^{11'}$, $R^{12'}$, $R^{13'}$, $R^{14'}$ and $R^{15'}$ are independently selected from H, ($C_1$–$C_6$)alkyl, aryl or aralkyl;

m is −2, −1, 0, +1 or +2 and the compound comprises a counterion when m is not 0;

the compound of formula (I) optionally being in the form of a dimer in which two L groups are linked either directly or through a group comprising one or more of ($C_1$–$C_6$)alkylene, ($C_1$–$C_6$)alkenylene, arylene, aralkylene, alkarylene, Se, Se—Se, S—S, N=N and C=O or in which L bears two Y groups and two Y' groups.

14. Process for preparing the compound of claim 1 which comprises the reaction of a compound of formula [($\eta^6$-$C_6$($R^1$)($R^2$)($R^3$)($R^4$)($R^5$)($R^6$))$RuX_2$], optionally in the form of a dimer, with Y-L-Y', in a suitable solvent for the reaction, wherein $R^1$, $R^2$, $R^3$, $R^4$, $R^5$, $R^6$, X, Y, Y' and L are as defined in claim 1.

* * * * *